United States Patent
Deshpande et al.

(10) Patent No.: US 8,841,296 B2
(45) Date of Patent: Sep. 23, 2014

(54) SUBSTITUTED 1,4-DIOXA-8-AZASPIRO[4,5]DECANES USEFUL AS FUNGICIDES AND A PROCESS FOR THE PREPARATION THEREOF

(75) Inventors: Mukund Vinayak Deshpande, Pune (IN); Sunita Ranjan Deshpande, Pune (IN); Fazal Shirazi, Pune (IN); Preeti Madhukar Chaudhary, Pune (IN); Nelavelli Malleswara Rao, Navi Mumbai (IN); Baidyanath Mohanty, Navi Mumbai (IN); Nageshwar Nath Sharma, Chandigarh (IN); Anand Kumar Bachhawat, Chandigarh (IN); Ganesan Kaliannan, Chandigarh (IN); Sanjoy Paul, Chandigarh (IN); Raj Kumar, Chandigarh (IN); Bommena Vittal Rao, Hydrabad (IN); Bhimrao Bodhanrao Gawali, Hydrabad (IN); Vaddu Venkata Narayana Reddy, Hydrabad (IN); Jhillu Singh Yadav, Hydrabad (IN)

(73) Assignee: Council of Scientific and Industrial Research, Anusandhan Bhawan, Rafi Marg, New Delhi (IN)

( * ) Notice: Subject to any disclaimer, the term of this patent is extended or adjusted under 35 U.S.C. 154(b) by 227 days.

(21) Appl. No.: 13/260,720

(22) PCT Filed: Mar. 23, 2010

(86) PCT No.: PCT/IB2010/000648
§ 371 (c)(1),
(2), (4) Date: Apr. 30, 2012

(87) PCT Pub. No.: WO2010/109299
PCT Pub. Date: Sep. 30, 2010

(65) Prior Publication Data
US 2012/0225877 A1    Sep. 6, 2012

(30) Foreign Application Priority Data
Mar. 27, 2009   (IN) .............. 612/DEL/2009

(51) Int. Cl.
*A01N 43/90* (2006.01)
*C07D 491/113* (2006.01)
*A01P 3/00* (2006.01)
*C07D 498/20* (2006.01)

(52) U.S. Cl.
CPC .................... *C07D 498/20* (2013.01)
USPC .......... 514/235.5; 514/278; 514/269; 544/70; 544/230; 546/19

(58) Field of Classification Search
CPC ..................... C07D 491/113; A01N 43/90
USPC ............. 514/235.5, 278, 269; 544/70, 230; 546/19
See application file for complete search history.

(56) References Cited

U.S. PATENT DOCUMENTS 4,548,639 A    10/1985   Riebel et al.
4,900,833 A *   2/1990   Robin et al. .............. 546/19

FOREIGN PATENT DOCUMENTS

| CH | 469736 A * | 4/1969 |
|---|---|---|
| DE | 19519710 A1 | 12/1996 |
| EP | 0023308 A1 | 2/1981 |
| EP | 0240398 A1 | 10/1987 |
| EP | 0621267 A1 * | 4/1994 |
| EP | 0833561 A1 | 4/1998 |
| JP | 49032542 B * | 8/1974 |
| JP | 5294972 A | 11/1993 |
| WO | WO 95/25106 A1 | 9/1995 |
| WO | WO 2005/054234 A2 | 6/2005 |
| WO | WO2005054234 A2 * | 6/2005 |

OTHER PUBLICATIONS

Denss et al. "Heterospiroalkanes" CH 469736A, published Apr. 30, 1969, Partial Machine Translation (English).*
Denss et al. "Heterospiroalkanes" CH 469736A, published Apr. 30, 1969, STN CAplus database entry (English).*
International Search Report from related PCT Patent Application No. PCT/IB2010/000648 mailed Sep. 28, 2010, application now published as WO 2010/109299 on Sep. 30, 2010.
Mertes et al., "Ketals and hemithioketals of 1-methyl-4-piperidone and tropinone", J. Pharm. Sci., vol. 20, No. 6, pp. 475-480 (1961).

* cited by examiner

*Primary Examiner* — Samantha Shterengarts
*Assistant Examiner* — Amanda L Aguirre
(74) *Attorney, Agent, or Firm* — King & Spalding LLP; Peter J. Dehlinger

(57) ABSTRACT

This invention provides novel substituted 1,4-dioxa-8-azaspiro[4,5]decane compounds of the general formula (1), wherein R1 is selected from phenethyl, 4,6-dimethoxypyrimidin-2-yl and (2-chloro-5-thiazolyl)methyl and R2 is selected from the group consisting of hydroxy, 4-bromo-2-chlorophenoxy, morpholin-4-yl, (2-chloro-5-thiazolyl)methyloxy, benzyloxy, phenylsulfanyl, benzotriazol and 5-chloro-2-fluoroanilino. The present invention also relates to a process for the preparation of novel substituted 1,4-dioxa-8-azaspiro[4,5]decanes of general formula (1). The novel substituted 1,4-dioxa-8-azaspiro[4,5]decane of general formula (1) has fungicidal activity.

22 Claims, No Drawings

SUBSTITUTED 1,4-DIOXA-8-AZASPIRO[4,5]DECANES USEFUL AS FUNGICIDES AND A PROCESS FOR THE PREPARATION THEREOF

This application is a U.S. National Stage of International Patent Application No. PCT/IB2010/000648, filed Mar. 23, 2010, which claims priority to Indian patent application No. 612/DEL/2009, filed Mar. 27, 2009, each of which is hereby incorporated by reference in its entirety.

FIELD OF THE INVENTION

This present invention relates to substituted 1,4-dioxa-8-azaspiro[4,5]decane general formula (1)

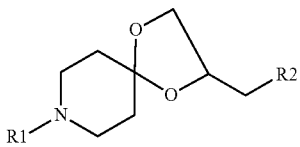

General formula (1)

wherein R1 is selected from the group consisting of alkyl(C1-C6), substituted alkyl (C1-C6) or substituted aryl (un) and substituted heteroaryl and R2 is selected from the group consisting of halo group, hydroxyl group, thio group, amino group, alkyl (C1-C6), substituted alkyl (C1-C6), substituted aryl (un) and substituted heteroaryl.

The present invention also relates to the process for the preparation of substituted 1,4-dioxa-8-azaspiro[4,5]decane of general formula (1).

The present invention further relates to fungicidal activity of substituted 1,4-dioxa-8-azaspiro[4,5]decane of general formula (1), their and compositions comprising them.

BACKGROUND OF THE INVENTION AND PRIOR ART

During the last decade, there has been tremendous increase in the frequency of fungal infections. The current fungicidal compounds that are widely used include triazole and strobilurin fungicides. But generally fungi develop resistance to antifungal agents easily, so also with the triazoles and strobilurins. Therefore, there is an urgent need in the art to have compounds to which fungi are not resistant. Also, the newly synthesized compounds should show fungicidal effect with high efficacy and low toxicity.

References may be made to patent application EP0833561, wherein fungicidal agents combining A) 8-t-butyl-2-(N-ethyl-N-n-propylamino)-methyl-1,4-dioxaspiro[4,5]decane of formula (1), B) 1-(4-chlorophenyl)-4,4-dimethyl-3-(1,2,4,-triazol-1-yl-methyl)pentane-3-ol of formula (II) and C) a triazole derivative of formula (III) X=CH(OH) (triadimenol) (IIIa) or X=CO (triadimephon) (IIIb) having fungicidal properties is disclosed.

References may be made to patent application JP3158631, wherein dioxa-aza-(acetylphenyl)spirodecane. 1,4-Dioxa-8-aza-8-(4-acetylphenyl)spiro(4,5)decane of formula (I) as nonlinear optical materials comprising the spirodecane and compositions containing the spirodecane is disclosed.

References may be made to patent application U.S. Pat. No. 4,900,833, wherein titled "Asymmetrical ester derivatives of 1,4-dihydropyridine-3,5-dicarboxylic acid" relates to novel asymmetrical esters derived from 1,4-dihydropyridine-3,5-dicarboxylic acid, of formula 1, in which R1 represents a C1-C4 alkyl group, R2 represents a C1-C4 alkyl group, a benzyl group, a benzoyl group or a phenyl group optionally substituted by one or more C1-C4 alkoxy, C1-C4 alkyl, cyano, nitro, hydroxyl or trifluoromethyl groups or by one or more halogen atoms, and R3 and R4, which are identical or different, each represent the hydrogen atom, a nitro group or a chlorine atom, their optical isomers and diastereoisomers and also the corresponding addition salts are disclosed. They are used as antihypertensive.

To fulfill the need in the art for compounds that possess fungicidal activity and further to have fungicidal compounds to which the fungi have not developed resistance, the invention discloses compounds that are substituted 1,4-dioxa-8-aza-spiro[4,5]decane as fungicidal agents.

OBJECTIVE OF THE INVENTION

The main objective of the present invention is to provide substituted 1,4-dioxa-8-azaspiro[4,5]decane of general formula (1).

Another objective of the present invention is to provide a process for the preparation of substituted 1,4-dioxa-8-azaspiro[4,5]decane of general formula (1).

Yet another objective of the present invention is to provide substituted 1,4-dioxa-8-azaspiro[4,5]decane of general formula (1) having fungicidal activity.

Still another objective of the present invention is to provide formulations of said compounds to be used as fungicides.

SUMMARY OF THE INVENTION

Accordingly, the present invention provides substituted 1,4-dioxa-8-azaspiro[4,5]decane compounds of general formula 1

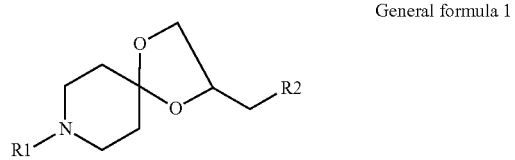

General formula 1 wherein R1 is selected from the group consisting of alkyl (C1-C6), substituted alkyl (C1-C6), or substituted aryl (unsaturated) and substituted heteroaryl and R2 is selected from the group consisting of halo group, hydroxyl group, thio group, amino group, alkyl (C1-C6), substituted alkyl (C1-C6), substituted aryl (unsaturated) and substituted heteroaryl.

In an embodiment, the present invention provides substituted 1,4-dioxa-8-azaspiro[4,5]decane compounds as claimed in claim 1, wherein R1 is selected from the group consisting of 2-phenethyl, 4,6-dimethoxypyrimidin-2-ylmethyl, (2-chlorothiazol-5-yl)methyl and R2 is selected from the group consisting of hydroxy, 4-bromo-2-chlorophenoxy, morpholin-4-yl (2-chloro-5-thiazolyl)methyloxy, benzyloxy; phenylsulfanyl, benzotriazol-1-yl and 5-chloro-2-fluoroanilino.

In yet another embodiment of the present invention, substituted 1,4-dioxa-8-azaspiro[4,5]decane compounds are represented by:
2-(4-bromo-2-chlorophenoxy)methyl-8-phenethyl-1,4-dioxa-8-azaspiro[4,5]decane (2);

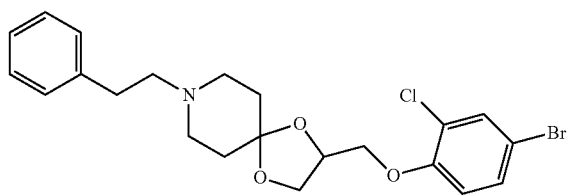 [SMILES: Clc1cc(Br)ccc1OCC1COC2(CCN(CCc3ccccc3)CC2)O1]

2-(morpholin-4-yl)methyl-8-phenethyl-1,4-dioxa-8-aza-spiro[4,5]decane (3);

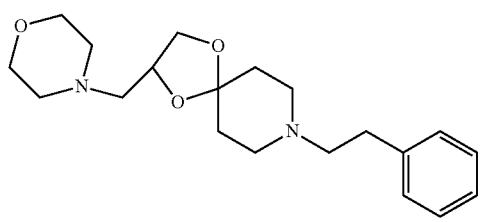 [SMILES: c1ccc(CCN2CCC3(CC2)OCC(CN2CCOCC2)O3)cc1]

2-(2-chloro-5-thiazolyl)methoxymethyl-8-phenethyl-1,4-dioxa-8azaspiro[4,5]decane (4);

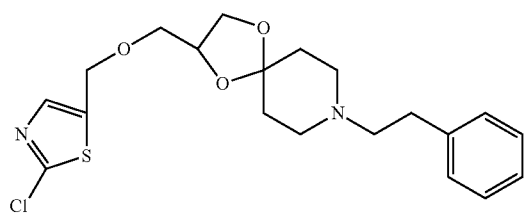 [SMILES: Clc1ncc(COCC2COC3(CCN(CCc4ccccc4)CC3)O2)s1]

2-benzyloxymethyl-8-phenethyl-1,4-dioxa-8-azaspiro[4,5]decane(5);

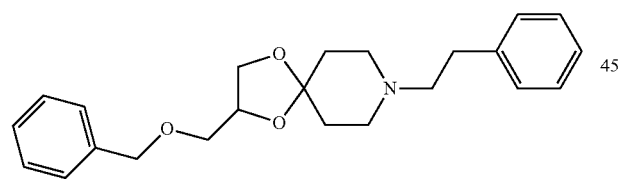

8-phenethyl-2-phenylsulphanylmethyl-1,4-dioxa-8-azaspiro[4,5]decane (6);

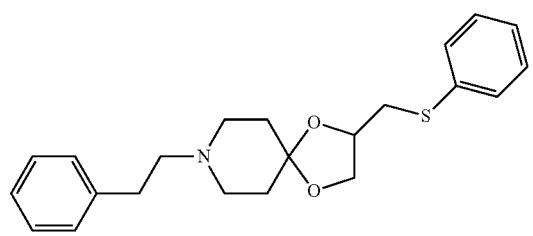 [SMILES: c1ccc(CCN2CCC3(CC2)OCC(CSc2ccccc2)O3)cc1]

2-(benzotriazol-1-yl)methyl-8-(4,6-dimethoxy-pyrimidin-2-yl)-1,4-dioxa-8-azaspiro[4,5]decane (7) and

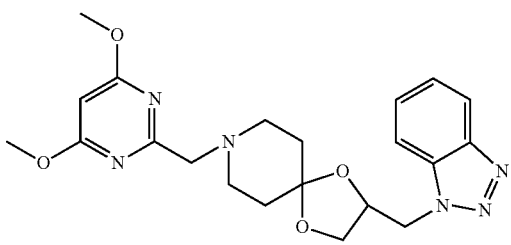 [SMILES: COc1cc(OC)nc(CN2CCC3(CC2)OCC(Cn2nnc4ccccc42)O3)n1]

N-(5-chloro-2-fluorophenyl)-N-[8-[(2-chloro-5-thiazolyl)methyl]-1,4-dioxa-8-azaspiro[4,5]dec-2-yl]methanamine (8)

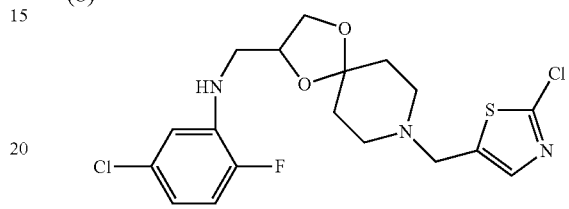

In yet another embodiment of the present invention, process for the preparation of compounds (2) to (6) of general formula 1 is provided and said process comprises the steps of:
i. providing compound 2-hydroxymethyl-8-phenethyl-1,4-dioxa-8-azaspiro[4,5]decane(1);

(1)

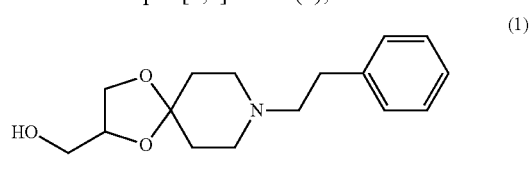

ii. reacting the compound 2-hydroxymethyl-8-phenethyl-1,4-dioxa-8-azaspiro[4,5]decane (1) as provided in step (i) with a reagent selected from the group consisting of 2-chloro-4-bromophenol, morpholine, 2-chloro-5-chloromethyl-thiazole, benzyl chloride, and thiophenol, in the presence of catalyst in an organic solvent to obtain a reaction mixture;
iii. stirring the reaction mixture as obtained in step (ii) at a temperature in the range of 25-120° C. for a period of 10 to 20 hrs;
iv. cooling the solution as obtained in step (iii) to a temperature of 25-30° C.;
v. filtering, purifying the cooled solution as obtained in step (iv) by known method to obtain the desired compounds of formula (2) to (6), In yet another embodiment of the present invention, compound 2 is obtained with reagent 2-chloro-4-bromophenol.

In yet another embodiment of the present invention, compound 3 is obtained with reagent morpholine.

In yet another embodiment of the present invention, compound 4 is obtained with reagent 2-chloro-5-chloromethyl-thiazole.

In yet another embodiment of the present invention, compound 5 is obtained with reagent benzyl chloride.

In yet another embodiment of the present invention, compound 6 is obtained with reagent thiophenol.

In yet another embodiment of the present invention, the catalyst used in step (ii) for the preparation of compounds 4 and 5 is tetrabutylammonium bromide (TBAB).

In yet another embodiment of the present invention, the catalyst used in step (ii) for the preparation of compounds 2, 3 and 6 is para toluene sulfonic acid (PTSA).

In yet another embodiment of the present invention, the reaction for the preparation of compounds 4 and 5 in step (ii) is carried out in the presence of sodium hydride.

In yet another embodiment of the present invention, a process for preparation of compounds (7) of general formula (1) is disclosed, and said process comprises the steps of:
I. passing dry HCl gas into the solution of N-(4,6 dimethoxy pyrimidin-2-yl)-4-piperidone and glycerol in DMF to obtain the compound 2-chloromethyl-8-(4, 6-dimethoxy-pyrimidin-2-yl)-1,4-dioxa-8-azaspiro[4, 5]decane;
II. reacting 2-chloromethyl-8-(4,6-dimethoxy-pyrimidin-2-yl)-1,4-dioxa-8-azaspiro[4,5]decane as obtained in step (I) with benzotriazole in the presence of potassium carbonate, under stirring, at a temperature of 100-150° C., for a period of 20-30 hrs;
III. cooling the stirred solution as obtained in step (II) to a temperature of 25-30° C. and distilling solvent to obtain the compound 2-(benzotriazol-1-yl)methyl-8-(4,6-dimethoxy-pyrimidin-2-yl)-1,4-dioxa-8-azaspiro[4,5] decane (7).

In yet another embodiment of the present invention, a process for the preparation of compounds (8) of general formula (1) is disclosed and said process comprises the steps of:
(a) passing dry HCl gas into the solution of 2-hydroxymethyl-8-(2-chloro-5-thiazolyl)methyl-1,4-dioxa-8-azaspiro[4,5]decane, in DMF to obtain the 2-chloromethyl-8-(2-chloro-5-thiazolyl)methyl-1,4-dioxa-8-azaspiro [4,5]decane;
(b) reacting the above said resultant compound with 5-chloro-2-fluoroaniline in the presence of potassium carbonate and potassium iodide, under stirring, at a temperature of 100-150° C., for a period of 20-30 hrs,
(c) cooling the stirred solution as obtained in step (II) to a temperature of 25-30° C. and distilling solvent to obtain the compound N-(5-chloro-2-fluorophenyl)-N-{8-(2-chloro-5-thiazolyl)methyl-1,4-dioxa-8-azaspiro[4,5] dec-2-yl}methanamine (8).

In yet another embodiment of the present invention, substituted 1,4-dioxa-8-azaspiro[4,5]decane compounds are fungicidal.

In yet another embodiment of the present invention, substituted 1,4-dioxa-8-azaspiro[4,5]decane compounds are showing fungicidal activity against wide range of fungi selected from the group consisting of, but not limited to *Pyricularia oryazae, Rhizoctonia solani, Pythium aphanidematum, Dreshlera oryazae, Collatrotrieum capsicum, Fusarium oxysporum* and *Magnaportha grisea*.

In yet another embodiment of the present invention, substituted 1,4-dioxa-8-azaspiro[4,5]decane compounds show 40-100% inhibition against all the test pathogens.

In yet another embodiment of the present invention, formulation for fungicidal activity comprises at least one active compound of general formula (1)

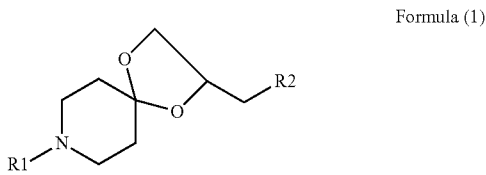

Formula (1)

wherein R1 is selected from the group consisting of alkyl with 1 to 6 carbon atoms, substituted alkyl (1-6), or substituted aryl (un) and substituted heteroaryl and R2 is selected from the group consisting of halo group, hydroxyl group, thio group, amino group, alkyl (C1-C6), substituted alkyl (C1-C6), substituted aryl (un), and substituted heteroaryl.

In yet another embodiment of the present invention, the formulation comprises
a) at least one active compound of general formula (1)

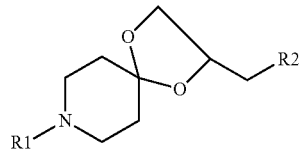

Formula (1)

wherein R1 is selected from the group consisting of alkyl with 1 to 6 carbon atoms, substituted alkyl (1-6), or substituted aryl (un) and substituted heteroaryl and R2 selected from the group consisting of halo group, hydroxyl group, thio group, amino group, alkyl (C1-C6), substituted alkyl (C1-C6), substituted aryl (un), and substituted heteroaryl, wherein said formulation is selected from the group consisting of Emulsifiable Concentrate (EC), Suspension Concentrate (SC) or Water Dispersible Granules (WDG).

In yet another embodiment of the present invention, Emulsifiable Concentrate (EC) is formulated as:
a) active ingredient 20-25%
b) emulsifier 10-20 wt % and
c) an organic solvent 60-70 wt %.

In yet another embodiment of the present invention, emulsifier used is a mixture of calcium dodecylbenzene sulfonate and styrinated ethoxylated phenol in the ratio of 3:7.

In yet another embodiment of the present invention, organic solvent used is selected from the group consisting of toluene, N-methylpyrrolidinone, cyclohexanone and C-IX (petroleum fraction).

In yet another embodiment of the present invention, Suspension Concentrate (SC) is formulated as:
a) Active ingredient (a.i.) 3% to 72%
b) Dispersing agent/
c) Suspending agent 3 to 15%
d) Wetting agent 1% to 2%
e) Anti freezing agent 5% to 15%
f) Anti fungal agent 0.05% to 0.2%
g) Anti foam agent 0.2% to 1.0%
h) Thickening agent(s) 0.1% to 1.0%
i) Demineralized water: Balance In yet another embodiment of the present invention, Water Dispersible Granules (WDG) is formulated as:
a) active ingredient 2.5% to 90%
b) dispersing/suspending agent 3% to 15%
c) wetting agent 1% to 3%
d) anti foam agent 0.2% to 1.0%
e) precipitated silica (for free flowing) 1% to 4%
f) china clay (filler) Balance

DETAILED DESCRIPTION OF THE INVENTION

Present invention provides substituted 1,4-dioxa-8-azaspiro[4,5]decane of general formula (1), wherein R1 is selected from the group consisting of alkyl (C1-C6), substituted alkyl (C1-C6), substituted aryl (un) and substituted heteroaryl and R2 is selected from the group consisting of halo group, hydroxyl group, thio group, amino group, alkyl (C1-C6), substituted alkyl (C1-C6), substituted aryl (un) and substituted heteroaryl.

The present invention further provides a process for the preparation of compound (1) to (6) of substituted 1,4-dioxa-8-azaspiro[4,5]decane of general formula (1) and the said process comprising the steps of
  a) passing dry HCl gas into N substituted-4-piperidone taken in toluene, followed by adding glycerol, at a temperature of 25-90° C. to obtain the compound 2-hydroxymethyl-8-phenethyl-1,4-dioxa-8-azaspiro[4,5]decane(1),
  b) reacting the compound 2-hydroxymethyl-8-phenethyl-1,4-dioxa-8-azaspiro[4,5]decane (1) with a reagent selected from 2-chloro-4-bromophenol, morpholine, 2-chloro-5-chloromethylthiazole, benzyl chloride, and thiophenol, in the presence of catalyst selected from para toluenesulfonic acid (PTSA) and tetrabutylammonium bromide (TBAB), in organic solvent, under stirring, at a temperature in the range of 25-120° C., for a period of 10 to 20 hrs, followed by cooling to a temperature of 25-30° C., filtration and purification by known method to obtain the desired compounds of formula 2-6.

The present invention further provides a process for the preparation of compound (7) of substituted 1,4-dioxa-8-azaspiro[4,5]decane of general formula (1) and the said process comprising the steps of
  passing dry HCl gas into the solution N-(4,6-dimethoxy-pyrimidin-2-yl)-4-piperidone and glycerol in DMF to obtain the compound 2-chloromethyl-8-(4,6-dimethoxy-pyrimidin-2-yl)-1,4-dioxa-8-azaspiro[4,5]decane and reacting the above said resultant compound with benzotriazole, in the presence of potassium carbonate, under stirring, at a temperature of 100-150° C., for a period of 20-30 hrs, followed by cooling up to 25-30° C. and distilling of the solvent to obtain the compound 2-(benzotriazol-1-yl)methyl-8-(4,6-dimethoxy-pyrimidin-2-yl)-1,4-dioxa-8-azaspiro[4,5]decane (7).

The present invention further provides a process for the preparation of compound (8) of substituted 1,4-dioxa-8-azaspiro[4,5]decane of general formula (1) and the said process comprising the steps of
  passing dry HCl gas into the solution 2-hydroxymethyl-8-(2-chloro-5-thiazolyl)methyl)-1,4-dioxa-8-azaspiro[4,5]decane, methanol in DMF to obtain the 2-chloromethyl-8-(2-chloro-5-thiazolyl)methyl-1,4-dioxa-8-azaspiro[4,5]decane and reacting the above said resultant compound with 5-chloro-2-fluoroaniline, in the presence of potassium carbonate and potassium iodide, under stirring, at a temperature of 100-150° C., for a period of 20-30 hrs, followed by cooling up to 25-30° C. and distilling of the solvent to obtain the compound N-(5-chloro-2-fluorophenyl)-N-{8-(2-chloro-5-thiazolyl)methyl-1,4-dioxa-8-azaspiro[4,5]dec-2-yl}methanamine (8).

The catalyst used in step (b) for the preparation of compounds 1, 4 and 5 is tetrabutylammonium bromide (TBAB).

The catalyst used in step (b) for the preparation of compounds 2, 3 and 6 is para toluenesulfonic acid (PTSA).

The reaction for the preparation of compound 4 and 5 in step (b) is carried out in the presence of sodium hydride.

The fungicidal compounds of the invention are formulated as Emulsifiable Concentrate (EC), Suspension Concentrate (SC) and Water Dispersible Granules (WDG).

The formulation comprises at least one active compound of general formula (1).

The emulsion concentrate (EC) of the invention was formulated as exemplified herein
Active ingredient: 20-25%
Emulsifier: 10-20 wt %
An organic solvent: 60-70 wt %

The emulsifier used is a mixture of calcium dodecylbenzene sulfonate and styrinated ethoxylated phenol in the range of 3:7.

The organic solvent used, is selected from the group consisting of N-methylpyrrolidinone, cyclohexanone and C-IX (petroleum fraction).

The water dispersible granules (WDG) of the invention was formulated as exemplified herein

| Active ingredient (a.i.) | 2.5% to 90% |
| Dispersing/suspending agent | 3% to 15% |
| Wetting agent | 1% to 3% |
| Anti foam agent | 0.2% to 1.0% |
| Precipitated silica (for free flowing) | 1% to 4% |
| China clay (filler) | Balance |
| | 100% w/w |

The dispersing/suspending agent is polycondensate of sodium methylnaphthalene and formaldehyde. The wetting agent is anionic surfactant belonging to sulphated fatty alcohol class. The anti foam agent is dimethylpolysiloxane.

The Suspension Concentrate (SC) of the invention was formulated as exemplified herein

| Active ingredient (a.i.) | 3% to 72% |
| Dispersing agent/Suspending agent | 3 to 15% |
| Wetting agent | 1% to 2% |
| Anti freezing agent | 5% to 15% |
| Anti fungal agent | 0.05% to 0.2% |
| Anti foam agent | 0.2% to 1.0% |
| Thickening agent(s) | 0.1% to 1.0% |
| Demineralized water | Balance |
| | 100% w/w |

The anti freezing agent is propylene glycol and the thickening agent is gum heteropolysaccharide, preferably xanthan gum and the anti fungal agent is 1,2-benzisothiazolin-3-one

EXAMPLES

The present invention will be more specifically explained by following examples. However, the scope of the present invention is not limited to the scope of these examples below.

Example 1

Preparation of 2-hydroxymethyl-8-phenethyl-1,4-dioxa-8-azaspiro[4,5]decane (Compound 1)

50 gm (0.2463 mole) of N-2-phenethyl-4-piperidone was taken in 300 ml toluene. To this 100 gm HCl gas was passed to make N-2-phenethyl-4-piperidone hydrochloride. Added 27 gram of glycerol slowly at room temperature 25° C. to 75° C. in presence of 4.6 gram of catalyst Para toluene sulfonic acid (PTSA). Reaction mixture was heated to 115° C. for 14 hrs. After cooling, the product was filtered. It was then neutralized and extracted with ethyl acetate. The solvent was distilled off to obtain the cream colored solid product with melting point of 96° C. and 94% yield.

Example 2

Preparation of 2-(4-bromo-2-chlorophenoxy)methyl-8-phenethyl-1,4-dioxa-8-azaspiro[4,5]decane (Compound 2)

2-hydroxymethyl-8-phenethyl-1,4-dioxa-8-azaspiro[4,5]decane (compound 1, 50 gm, 0.18 mole) was dissolved in toluene (300 ml) at room temperature. To this 44 gms of 2-chloro-4-bromophenol in toluene (150 ml) was added at room temperature 28° C. in the presence of ParaToluene-sulfonic Acid (PTSA, 3.5 gm). Reaction mixture was refluxed with stirring for 13 hrs. It was then cooled and filtered. The filtrate was given water wash to bring the pH to neutral. Toluene was removed under vacuum to obtain a thick brick red colored product 95% yield.

Example 3

Preparation of 2-(morpholin-4-yl)methyl-8-phenethyl-1,4-dioxa-8-azaspiro[4,5]decane (Compound 3)

2-hydroxymethyl-8-phenethyl-1,4-dioxa-8-azaspiro[4,5]decane (Compound 1.50 gm, 0.18 mole), Para Toluene-sulfonic Acid (PTSA, 3.5 gms) was dissolved in toluene (300 ml) at 28° C. To this was added 18.5 gm of morpholine drop wise with continuous stirring, continued the stirring for 13 hrs at reflux temperature. Toluene was distilled under vacuum to get a semi-solid with brick red color. The yield of the product was 90%.

Example 4

Preparation of 2-(2-chloro-5-thiazolyl)methoxymethyl-8-phenethyl-1,4-dioxa-8-azaspiro[4,5]decane (Compound 4)

To 8.64 g (0.36 mole) of sodium hydride in toluene (250 ml) was added 2-hydroxymethyl-8-phenethyl-1,4-dioxa-8-azaspiro[4,5]decane (compound 1.50 gm, 0.18 mole) in toluene (350 ml) with stirring at 28° C. The phase transfer catalyst tetrabutylammonium bromide TBAB 2 gm was added and 31 gm of 2-chloro-5-chloromethylthiazole in toluene (225 ml) was then added drop wise at 10° C. and the reaction mixture was refluxed for 15 hrs. The reaction mixture was washed with water and the product was extracted with methylene chloride 100 ml. The solvent was distilled off to get thick dark colored liquid. The yield of the product was 85%.

Example 5

Preparation of 2-benzyloxymethyl-8-phenethyl-1,4-dioxa-8-azaspiro[4,5]decane (Compound 5)

2-hydroxymethyl-8-phenethyl-1,4-dioxa-8-azaspiro[4,5]decane (compound 1, 50 gm, 0.18 mole) was dissolved in toluene (250 ml) at room temperature. 10 gm of 60% of sodium hydride in toluene (300 ml) was added to the above solution until the effervescence ceased. 2 gram of phase transfer catalyst tetrabutylammonium bromide (TBAB) was added. Benzyl chloride, 23 gm was then added drop wise to the above reaction mass and the reaction was maintained at 58° C. for 15 hrs. The reaction mass was poured into water and organic layer was separated. Toluene was removed under reduced pressure to get a thick reddish brown liquid. The yield is 84%.

Example 6

Preparation of 8-phenethyl-2-phenylsulphanylmethyl-1,4-dioxa-8 azaspiro[4,5]decane (Compound 6)

2-hydroxymethyl-8-phenethyl-1,4-dioxa-8-azaspiro[4,5]decane (Compound 1, 50 gm, 0.18 mole) and Para Toluene-sulfonic Acid (PTSA, 2 gm) were dissolved in toluene (350 ml) at room temperature. 20 gm of thiophenol was added drop wise to the above solution. The reaction was refluxed for 13 hrs at reflux temperature. The solvent was distilled off to get the light brown solid product with a melting point of 58° C. The yield of the product was 95%.

Example 7

Preparation of 2-hydroxymethyl-8-(4,6-dimethoxy-pyrimidin-2-yl)-1,4-dioxa-8-azaspiro[4,5]decane (Starting Material for the Preparation of Compound 7)

25 g of piperidone hydrochloride was slowly added in lots to 2 g of TBAB and 67 g of K2CO3 in 250 ml of acetonitrile at 50-60° (provide exact value), then 25 g of piperidone hydrochloride was slowly added in lots and the reaction mixture stirred for 1 hr. 29 g of 4,6-dimethoxy-2-chloropyrimidine was added slowly over a period of 1 hr and the reaction mixture was refluxed for 11 hours at 60° C.

The reaction mixture was neutralized with aq.NaOH solution and extracted with MDC, (methylene dichloride). Organic layer was distilled off to get 1-(4-6-dimethoxy-pyrimidin-2-yl)-piperidin-4-one.

45 g of 1-(4-6-dimethoxy-pyrimidin-2-yl)-piperidin-4-one. and 5.2 g of PTSA were stirred in toluene (400 ml) for half an hour. 21 g Glycerol (1.2 mole) was added drop wise and the reaction mixture was refluxed at 120° C. for 7 hours. Toluene was removed to get the desired product with 85% yield.

Example 8

Preparation of 2-chloromethyl-8-(4,6-dimethoxy-pyrimidin-2-yl)-1,4-dioxa-8-azaspiro[4,5]decane (Intermediate for Compound 7)

20 g (0.064 mole) of 2-hydroxymethyl-8-(4,6-dimethoxy-pyrimidin-2-yl)-1,4-dioxa-8-azaspiro[4,5]decane was taken in DMF (250 ml) and 50 gram of dry HCl gas was passed into the reaction mass over a period of 3 hrs at −10 to 0° C. and stirred for 1.0 hr to get the required chloromethyl compound. 90% yield.

Example 9

Preparation of 2-(benzotriazol-1-yl)methyl-8-(4,6-dimethoxy-pyrimidin-2-yl)-1,4-dioxa-8-azaspiro[4,5]decane (Compound 7)

To 37.63 gm (0.3163 mole) of benzotriazole and 35 gm of potassium carbonate in Dimethylformamide (DMF) (350 ml) was added slowly under stirring 82 gm of 2-chloromethyl-8-(4,6-dimethoxy-pyrimidin-2-yl)-1,4-dioxa-8-azaspiro[4,5]decane (intermediate for compound 7) in DMF (300 ml). After the addition, reaction mixture was heated to 120° C. and maintained for 30 hrs. The reaction mixture was cooled to room temperature 28° C. and filtered. The solvent was distilled off to get the product. It was a thick dark brown liquid. Yield of product was 90%

Compound 2-chloro-5-chloromethylthiazole is known. Ref. Ref. 137:33289 Miyazaki, Takashi; Satou, Makoto; Inoue, Yoshihisa (Takeda Chemical Industries, Ltd., Japan). U.S. Pat. No. 6,407,251 B1 18 Jun. 2002, 4 pp. (English). (United States of America). CODEN: USXXAM. CLASS: ICM: C07D277-20. NCL: 548202000. APPLICATION: US 2001-4829 7 Dec. 2001. PRIORITY: JP 2000-400802 28 Dec. 2000. DOCUMENT TYPE: Patent CA Section: 28 (Heterocyclic Compounds (More Than One Hetero Atom)) Section cross-reference(s): 45

Example 10

Preparation of 1-(2-chloro-5-thiazolylmethyl)piperidine 4-one 25 gm of piperidone hydrochloride was taken in 250 ml acetonitrile. 68.7 gm of $K_2CO_3$ was added under stirring at 60° C., followed by addition of 27.8 gm of 2-chloro-5-chloromethylthiazole and refluxed for 6 hours.

Example 11

Preparation of N-(5-chloro-2-fluorophenyl)-N-{8-(2-chloro-5-thiazolyl)methyl-1,4-dioxa-8-aza-spiro[4,5]dec-2-yl}methanamine (Compound 8)

21 gm (0.065 mole) of 2-chloromethyl-8-(2-chloro-5-thiazolyl)methyl-1,4-dioxa-8-azaspiro[4,5]decane was taken in DMF (300 ml) at 28° C. To this mixture was added 28 gm of potassium carbonate, 10 gm of 5-chloro-2-fluoroaniline and the catalyst potassium iodide. The mass was kept at 140° C. for 20 hrs. The mixture was poured into ice-cooled water and the mass was extracted with ethyl acetate. The solvent was distilled off to get the dark brick red colored product with yield 85%.

Example 12

20 gram of active compound (1), 10 gram of emulsifier made of calcium dodecylbenzene sulfonate (3 gram) and styrinated ethoxylated phenol (7 gram) were taken in 70 gram C-IX (Petroleum fraction) and stirred well for 60 minutes to get the respective formulated product. Yield 100 gram.

Example 13

Charge 49.4 g water in a container. Add 0.5 g defoamer & stirred. Add 4 g dispersing & 1 g wetting agent under stirring. Add 10 g anti freezing agent under stirring. Add 0.1 g anti fungal agent under stirring. Add 25 g active ingredient (as 100% basis) & homogenize for 30 minutes. Pass above pre mix thro' Dyno mill till get desire particle size. Collect the milled material in a container. Add 10 g of 2% thickening agent & stir slowly for 30 minutes.

Example 14

Blende 50 g active ingredient (as 100% basis), 7 g dispersing/suspending agent, 2 g wetting agent, 0.2 g anti foam agent, 3 g precipitated silica and 37.8 g China clay. Grind blended material on Air jet mill. Add 15 g water in air jet material & make dough in Sigma mixer. Pass the dough thro' die roller extruder. Collect extruded granules and dry in dryer. Sieve the dried granules. Pack the material after getting clearance from QA.

Example 15

Fungicidal Activity Materials and Methods

*Fusarium oxysporunz, Magnaporthe grisea, Pyrricularia oryzae* and *Pythium aphanidermatum* were maintained on potato dextrose agar slants at 28° C. *Rhizoctonia solani, Colletotrichum capsici, Drechslera oryzae* were maintained on czapek dox agar slants at 28° C. *R. solani, C. capsici, D. oryzae, F. oxysporum, M. grisea. P. oryzae* and *P. aphanidernzatum* were inoculated in potato dextrose broth at 28° C. for 48 hr. Compounds were solubilized in DMSO (2.5% v/v) and stock solution of 1.28 mg/ml was prepared.

Growth Inhibition Plate Assay 2 liters of potato dextrose medium was prepared and 200 ml dispensed per 500 ml Erlenmeyer's flask and sterilized. Stock solutions of 12.5, 25 and 37.5 mg of the test compound (100% purity) were prepared in 5 ml standard flasks separately. The compound was dissolved using suitable solvent (2.5% v/v DMSO) and volume made up. This gives a concentration of 2500, 5000 and 7500 ppm respectively. 1 ml of stock solution was transferred to 100 ml of the medium while sterilized medium is molten to obtain the required concentrations of 25, 50 & 75 ppm from 2500, 5000 and 7500 ppm stock solution, respectively. The medium was distributed equally into the petri plates and allow the medium to solidify. The suitable number of replications for each treatment was maintained. The actively growing test organisms were taken in petri plates. Small uniform discs of the test fungal culture were cut using sterile cork borer (7 mm) and each one of them were transferred aseptically to the centre of petri plates. The solvent control was maintained by adding 2.5% of solvent used in the experiment to the media and pouring into the plate. Suitable checks were maintained by transferring discs of test organisms to petri plates containing medium without the compound or the solvent. Both the treated plates and control plates were incubated at 28° C. The colony diameter was measured at 24 hour intervals and mean values calculated.

Fungicidal Activity

All the synthesized compounds were evaluated for fungicidal activity against plant pathogenic fungi and all were found to be active. Compound 7 exhibited 40-60% of inhibition against *R. solani, F. oxysporum* and *P. aphanidermatum*, whereas compound 8 showed 50-60% inhibition against *P. aphnidermatum*. Compound 5 exhibited 40-50% inhibition against *R. solani* and *F. oxysporum*, whereas 60-70% against *D. oryzae* and *M. grisea*. Compound 4 showed 20-30% of inhibition against all the tested strains. Compounds 2 and 6 were found to be active against all pathogens.

Compound 2 showed 90-100% inhibition against all the test pathogens where as, compound 6 inhibited 90-100% growth of *Rhizoctonia solani* and 60-90% that of *C. capsici, D. oryzae, F. oxysporum* and *P. oryzae*. Compound 3 registered 70-80% inhibition of *R. solani, F. oxysporum;* 60-70% of *D. oryzae* and 40-50% of *P. oryzae*.

TABLE 1

In vitro fungicidal activities of compounds

| Comps No. | Plate assay with Plant pathogenic Fungi (25 ppm) | | | | | |
|---|---|---|---|---|---|---|
| | P1 | P2 | P3 | P4 | P5 | P6 |
| C2 | 90-100 | 90-100 | 90-100 | 90-100 | 90-100 | 90-100 |
| C3 | 70-80 | ND | 60-70 | 70-80 | 40-50 | ND |
| C4 | 20-30 | 20-30 | ND | 30-40 | 30-40 | ND |
| C5 | 40-50 | 20-Oct | 60-70 | 40-50 | ND | ND |
| C6 | 90-100 | 60-70 | 70-80 | 70-80 | 80-90 | 50-60 |
| C7 | 40-50 | 30-40 | 20-Oct | 40-50 | ND | 50-60 |
| C8 | 20-Oct | ND | 20-Oct | 20-30 | ND | 50-60 |

ND—Not Detectable.

P1 *R. solani*; P2 *C. capsici*; P3 *D. oryzae*; P4 *F. oxysporum*; P5 *P. oryzae*; P6 *P. aphanidermatum*

Example 14

Fungicidal Efficacy of Compounds Against Grape Powdery Mildew

A field experiment was conducted on pruned grapevine, in a randomized block design with ten treatments (Table No 1) and three replications. Two sprays were given at an interval of 10 days. The plot size was eight vines per treatment/replication. The spraying was done by Knapsack sprayer using 850 L spray volume/hectare.

The observations on powdery mildew incidence were recorded at 11 and 15 days after second spray from 10 randomly selected bunches/treatment/replication by counting total number of berries and number of downy mildew infected berries. Based on the observations percent incidence was worked out. The data was subjected to statistical analysis and presented in the Table 2.

TABLE NO 2

Efficacy of compounds, 2, 20% EC and 6, 20% EC in comparison with standards against grape powdery mildew.

| Treatment | PDI* on Bunches 11 DAIIS* | % Disease Control | PDI on Bunches 15 DAIIS | % Disease Control |
|---|---|---|---|---|
| Compound 2 @ 340 g a.i./ha | 12.96 | 56.67 | 10.23 | 60.84 |
| Compound 2 @ 510 g a.i./ha | 13.6 | 54.53 | 9.6 | 63.26 |
| Compound 2 @ 680 g a.i./ha | 12.48 | 58.27 | 8.9 | 65.93 |
| Compound 6 @ 340 g a.i./ha | 11.89 | 60.24 | 10.6 | 59.43 |
| Compound 6 @ 510 g a.i./ha | 10.09 | 66.26 | 9.1 | 65.17 |
| Compound 6 @ 680 g a.i./ha | 9.09 | 69.6 | 7.65 | 70.72 |
| Hexaconazole 5 E @ 42.50 g a.i./ha | 8.59 | 71.28 | 4.81 | 81.59 |
| Kresoxim methyl 50 SC 425 g a.i./ha | 5.5 | 81.61 | 3.55 | 86.41 |
| Azoxystrobin 25 SC @ 212 g a.i./ha | 8.68 | 70.97 | 5.92 | 77.34 |
| Control (untreated check) | 29.91 | — | 26.13 | — |
| CD (Critical Difference) at 5% | 5.21 | | 4.55 | |

*PDI—Percent Disease Incidence, DAIIS—Days after 2$^{nd}$ Spray a) g.a.i/ha—gram active ingredient per hectare.

At 11 days after second spray Compound 6 20% EC @ 510 & 680 g a.i./ha (gram active ingredient/hectare) was observed at par with standards Hexaconazole 5% E @ 42.50 g a.i./ha, Kresoxim methyl 50% SC @ 425 g a. i./ha and Azoxystrobin 25% SC @ 212 g a. i./ha in reducing powdery mildew incidence in the range of 5.50 to 10.09% and recorded percent reduction over untreated check, 66.26 to 81.61%. Whereas, the untreated check recorded highest powdery mildew incidence of 29.91%.

At 15 days after second spray, Compound 6, 20% EC @ 680 g a. i./ha (gram active ingredient/hectare) was found comparable standards Hexaconazole 5% E 42.50 g a.i./ha, Kresoxim methyl 50% SC @ 425 g a. i./ha and Azoxystrobin 25% SC @ 212 g a. i./ha in reducing powdery mildew incidence in the range of 3.55 to 7.65%. The untreated check treatment registered highest powdery mildew incidence of 26.13%.

Example 16

Efficacy of Compounds in Comparison with Standards Against Grape Downy Mildew In this example, 2(20% EC), 6(20% EC) and mixture of 2 and 6 (3:1, 20% EC) were evaluated to find out their efficacy in controlling grape downy mildew in comparison with standards.

A field experiment was conducted on pruned grapevine, in a randomized block design with ten treatments (Table No. 3) and three replications. Two sprays were given at an interval of 6 days starting at 28 days after pruning. The plot size was ten vines per treatment/replication. The spraying was done by Knapsack sprayer using 1000 L spray volume/hectare.

The observations on downy mildew incidence were recorded from 10 randomly selected branches/treatment/replication by counting the total number of leaves and number of downy mildew infected leaves at 7 and 10 days after second spray. Based on the observations, percent disease incidence was worked out. The data was subjected to statistical analysis. The results on efficacy of the compounds against grape downy mildew are presented in Table No 3.

TABLE NO 3

Efficacy of compounds in comparison with standards against grape downy mildew

| Treatment | Grape Downy mildew | | | |
|---|---|---|---|---|
| | 7 DAIIS* | % Control | 10 DAIIS | % Control |
| Cpd 2 20% EC @ 400 g a.i./ha | 4.46 | 73.53 | 7.58 | 66.72 |
| Cpd 2 20% EC @ 800 g a.i./ha | 2.77 | 83.56 | 5.27 | 76.86 |
| Cpd 6 20% EC @ 400 g a.i./ha | 16.14 | 4.21 | 24.88 | 0 |
| Cpd 6 20% EC @ 800 g a.i./ha | 16.91 | 0 | 17.7 | 22.3 |
| Cpd2:6(3:1) 20% EC @ 400 g a.i./ha | 16.36 | 2.9 | 14.85 | 34.81 |
| Cpd2:6(3:1) 20% EC @ 800 g a.i./ha | 10.67 | 36.67 | 14.51 | 36.3 |
| Metalaxyl 8% + Mancozeb 64% 72 WP @ (80 + 640 g a.i./ha) | 6.01 | 64.33 | 6.58 | 71.11 |
| Azoxystrobin 23 SC @ 230 g a.i./ha | 3.32 | 80.29 | 2.7 | 88.14 |
| Dimethomorph 50 WP @ 500 g a.i./ha | 2.39 | 85.81 | 2.42 | 89.37 |
| Control (Untreated check) | 16.85 | — | 22.78 | — |
| CD at 5% | 4.72 | | 4.25 | |

15

TABLE NO 3-continued

Efficacy of compounds in comparison with
standards against grape downy mildew

| Treatment | Grape Downy mildew | | | |
|---|---|---|---|---|
| | 7 DAIIS* | % Control | 10 DAIIS | % Control |

*DAIIS—Days After 2nd Spray

Grape Downy Mildew (7 Days after 2$^{nd}$ Spray)

From the results presented in the Table No 3, it is evident that, both the doses of Compound 2, 20% EC @ 400 & 800 g a. i./ha were found comparable with standard check fungicides Metalaxyl 8%+Mancozeb 64% 72 WP @ (80+640 g a. i./ha), Azoxystrobin 23 SC @ 230 g a. i./ha and Dimethomorph 50 WP @ 500 g a. i./ha effective in controlling downy mildew and registered 2.39 to 6.01% incidence and reduction over untreated check 64.33 to 85.81%. The untreated check recorded highest downy mildew incidence of 16.85%.

Grape Downy Mildew (10 Days after 2$^{nd}$ Spray)

At 10 days after second spray, Compound 2, 20% EC @ 800 g a. i./ha was found to be at par with standard check fungicides, Metalaxyl 8%+Mancozeb 64% 72 WP @ (80+640 g a. i./ha), Azoxystrobin 23 SC @ 230 g a. i./ha and Dimethomorph 50 WP 500 g a. i./ha in controlling downy mildew and registered percent incidence in the range of 2.42 to 5.27. The untreated check recorded highest downy mildew incidence of 22.78%.

Example 17

Efficacy of Compounds in Comparison with Standards Against Rose Powdery Mildew A field experiment was conducted on rose variety in a randomized block design with ten treatments (Table No. 4) and three replications. Two sprays were given at an interval of 4 days. The spraying was done by Foot operated sprayer using 1200 L spray volume/hectare.

The observations on powdery mildew incidence were recorded from 10 randomly selected branches/treatment/replication by counting total number of leaves and number of powdery mildew infected leaves at 4 days after first spraying. Based on the observations percent incidence was worked out. The data was subjected to statistical analysis.

TABLE NO 4

Efficacy of compounds in comparison with
standards against rose powdery mildew

| Treatment | Rose PM % incidence & Control | |
|---|---|---|
| | 4 DAS* | % Control |
| Cpd 6 20% EC @ 240 g a.i./ha | 38.42 | 25.44 |
| Cpd 6 20% EC @ 480 g a.i./ha | 29.45 | 42.84 |
| Cpd 6 20% EC @ 720 g a.i./ha | 23.21 | 54.95 |
| Cpd2:6(3:1) 20% EC @ 720 g a.i./ha | 39.53 | 23.28 |
| Cpd 2 20% EC @ 720 g a.i./ha | 36.83 | 28.52 |
| Control (untreated check) | 51.53 | — |
| CD at 5% | 9.60 | |

*DAS—Days after Spray

It was evident from the results that, 6.20% EC @ 480 and 720 g a.i./ha was effective in minimizing the powdery mildew incidence in the range of 23.21 to 29.45% and recorded percent control over untreated check in the range of 42.84 to 54.31%, whereas, the untreated check recorded highest powdery mildew incidence of 51.53%.

ADVANTAGES OF THE INVENTION

The main advantage of the present invention is:
Substituted 1,4-dioxa-8-azaspiro[4,5]decane are useful as fungicidal compound alone or in combination.

We claim:

1. A substituted 1,4-dioxa-8-azaspiro[4,5]decane compound of general formula 1:

General formula 1

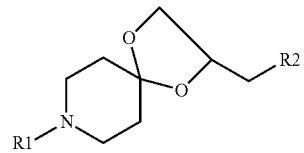

wherein R1 is selected from the group consisting of alkyl (C1-C6), substituted alkyl (C2-C6), —(CH$_2$)—R wherein R is thiazolyl or pyrimidinyl, substituted aryl, and substituted heteroaryl, and R2 is selected from the group consisting of, 4-bromo-2-chlorophenoxy, morpholin-4-yl, (2-chloro-5-thiazolyl)methyloxy, benzyloxy, phenylsulfanyl, benzotriazol and 5-chloro-2-fluoroanilino.

2. A substituted 1,4-dioxa-8-azaspiro[4,5]decane compounds as claimed in claim 1, wherein R1 is selected from the group consisting of 2-phenethyl, 4,6-dimethoxy pyrimidin-2-ylmethyl, and (2-chlorothiazol-5-yl)methyl, and R2 is selected from the group consisting of, 4 bromo-2-chlorophenoxy, morpholin-4-yl, (2-chloro-5-thiazolyl)methyloxy, benzyloxy, phenylsulfanyl, benzotriazol-1-yl, and 5-chloro-2-fluoroanilino.

3. A substituted 1,4-dioxa-8-azaspiro[4,5]decane compound as claimed in claim 1, wherein the compound-is selected from:

2-(4-bromo-2-chlorophenoxy)methyl-8-phenethyl-1,4-dioxa-8-azaspiro[4,5]decane (2);

(2)

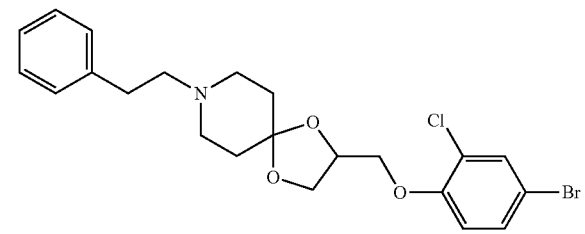

2-(morpholin-4-yl)methyl-8-phenethyl-1,4-dioxa-8-azaspiro[4,5]decane (3);

(3)

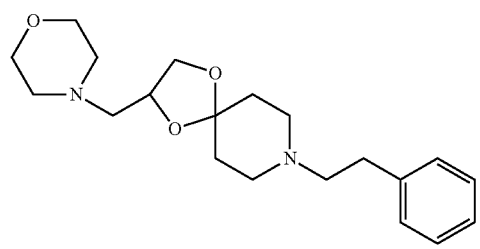

2-(2-chloro-5-thiazolyl)methoxymethyl-8-phenethyl-1,4-dioxa-8-azaspiro[4,5]decane (4);

(4)

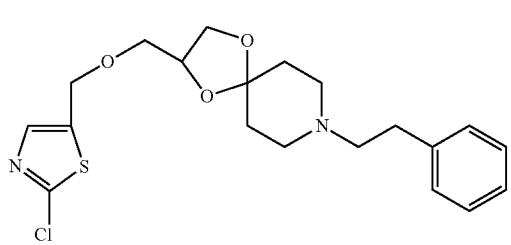

2-benzyloxymethyl-8-phenethyl-1,4-dioxa-8-azaspiro[4,5]decane (5);

(5)

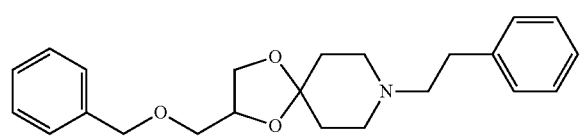

8-phenethyl-2-phenylsulphanylmethyl-1,4-dioxa-8-azaspiro[4,5]decane (6);

(6)

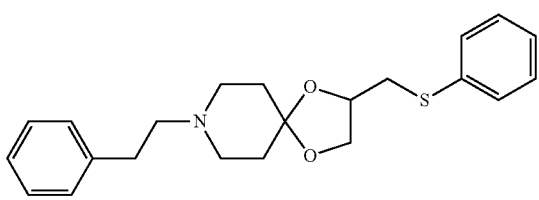

2-(benzotriazol-1-yl)methyl-8-(4,6-dimethoxy-pyrimidin-2-yl)-1,4-dioxa-8-azaspiro[4,5]decane (7);

(7)

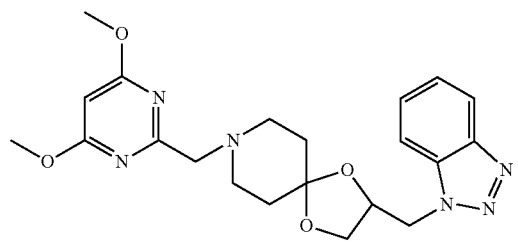

and N-(5-chloro-2-fluorophenyl)-N-[8-[(2-chloro-5-thiazolyl)methyl]-1,4-dioxa-8-azaspiro[4,5]dec-2-yl]methanamine (8)

(8)

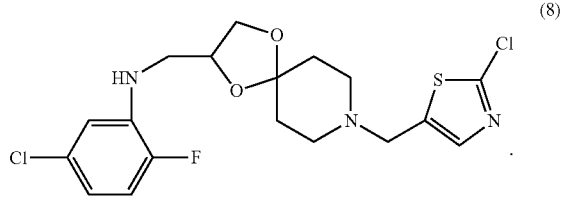 [SMILES: Fc1ccc(Cl)cc1NCC1COC2(CCN(Cc3cnc(Cl)s3)CC2)O1]

4. A process for the preparation of a compound selected from compounds (2) to (6) of general formula 1 of claim 3, said process comprising:
reacting the compound 2-hydroxymethyl-8-phenethyl-1,4-dioxa-8-azaspiro[4,5]decane (1)

(1)

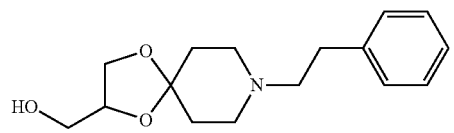

with a reagent selected from the group consisting of 2-chloro-4-bromophenol, morpholine, 2-chloro-5-chloromethyl-thiazole, benzyl chloride, and thiophenol, in the presence of catalyst in an organic solvent, at a temperature in the range of 25-120° C. for a period of 10 to 20 hrs.

5. A process as claimed in claim 4, wherein compound 2 is obtained, and the reagent is 2-chloro-4-bromophenol.

6. A process as claimed in claim 4, wherein compound 3 is obtained, and the reagent is morpholine.

7. A process as claimed in claim 4, wherein compound 4 is obtained, and the reagent is 2-chloro-5-chloromethyl-thiazole.

8. A process as claimed in claim 4, wherein compound 5 is obtained, and the reagent is benzyl chloride.

9. A process as claimed in claim 4, wherein compound 6 is obtained, and the reagent is thiophenol.

10. A process as claimed in claim 4, wherein the catalyst used for the preparation of compounds 4 and 5 is tetrabutylammonium bromide (TBAB).

11. A process as claimed in claim 4, wherein the catalyst used for the preparation of compounds 2, 3 and 6 is para toluene sulfonic acid (PTSA).

12. A process as claimed in claim 4, for the preparation of compounds 4 and 5, wherein said reacting is carried out in the presence of sodium hydride.

13. A process for preparation of compound (7) of general formula (1) of claim 3, said process comprising:
reacting 2-chloromethyl-8-(4,6-dimethoxy-pyrimidin-2-yl)-1,4-dioxa-8-azaspiro[4,5]decane with benzotriazole in the presence of potassium carbonate, under stirring, at a temperature of 100-150° C., for a period of 20-30 hrs.

14. A process for the preparation of compound (8) of general formula (1) of claim 3, said process comprising:
reacting 2-chloromethyl-8-(2-chloro-5-thiazolyl)methyl-1,4-dioxa-8-azaspiro[4,5]decane with 5-chloro-2-fluoroaniline, in the presence of potassium carbonate and potassium iodide, under stirring, at a temperature of 100-150° C., for a period of 20-30 hrs.

15. A substituted 1,4-dioxa-8-azaspiro[4,5]decane compound as claimed in claim 1, wherein said compound is fungicidal.

16. A formulation for fungicidal activity comprising at least one active compound of general formula (1)

Formula (1)

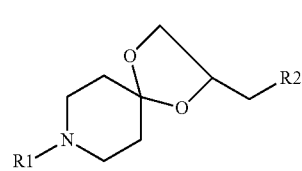

wherein R1 is selected from the group consisting of alkyl with 1 to 6 carbon atoms, substituted alkyl (2-6), —(CH$_2$)—R wherein R is thiazolyl or pyrimidinyl, substituted aryl, and substituted heteroaryl, and R2 is selected from the group consisting of halo group, hydroxyl group, thio group, amino group, alkyl (C1-C6), substituted alkyl (C1-C6), substituted aryl, and substituted heteroaryl.

17. A formulation as claimed in claim 16, wherein said formulation is in the form of an Emulsifiable Concentrate (EC), a Suspension Concentrate (SC), or Water Dispersible Granules (WDG).

18. The formulation as claimed in claim 17, wherein said Emulsifiable Concentrate (EC) is formulated as:
   a) active ingredient 20-25 wt %
   b) emulsifier 10-20 wt %, and
   c) organic solvent 60-70 wt %.

19. An Emulsion Concentrate (EC) as claimed in claim 18, wherein the emulsifier is a mixture of calcium dodecylbenzene sulfonate and styrenated ethoxylated phenol in the ratio of 3:7.

20. An Emulsion Concentrate (EC) as claimed in claim 18, wherein the organic solvent is selected from the group consisting of toluene, N-methylpyrrolidinone, cyclohexanone and C-IX (petroleum fraction).

21. The formulation as claimed in claim 17, wherein said Suspension Concentrate (SC) is formulated as:
   a) active ingredient 3% to 72% w/w
   b) dispersing agent
   c) suspending agent 3 to 15% w/w
   d) wetting agent 1% to 2% w/w
   e) anti freezing agent 5% to 15% w/w
   f) anti fungal agent 0.05% to 0.2% w/w
   g) anti foam agent 0.2% to 1.0% w/w
   h) thickening agent(s) 0.1% to 1.0% w/w
   i) demineralized water: Balance.

22. The formulation as claimed in claim 17, wherein said Water Dispersible Granules (WDG) are formulated as:
   a) active ingredient 2.5% to 90% w/w
   b) dispersing/suspending agent 3% to 15% w/w
   c) wetting agent 1% to 3% w/w
   d) anti foam agent 0.2% to 1.0% w/w
   e) precipitated silica 1% to 4% w/w
   f) china clay (filler): Balance.

* * * * *